US012661419B2

(12) United States Patent
Koppen et al.

(10) Patent No.: US 12,661,419 B2
(45) Date of Patent: Jun. 23, 2026

(54) STERILISATION DEVICE FOR STERILISING A SECTION OF A CATHETER TUBE AND A METHOD FOR STERILISING A SECTION OF A CATHETER TUBE

(71) Applicant: VIOBAC APS, Valby (DK)

(72) Inventors: Kasper Koppen, Valby (DK); Mads Orbæk Andersen, Frederiksberg (DK); Andrim Halili, Copenhagen S (DK)

(73) Assignee: VIOBAC ApS, Valby (DK)

( * ) Notice: Subject to any disclaimer, the term of this patent is extended or adjusted under 35 U.S.C. 154(b) by 1016 days.

(21) Appl. No.: 17/594,177

(22) PCT Filed: Apr. 3, 2020

(86) PCT No.: PCT/DK2020/050089
§ 371 (c)(1),
(2) Date: Oct. 5, 2021

(87) PCT Pub. No.: WO2020/200389
PCT Pub. Date: Oct. 8, 2020

(65) Prior Publication Data
US 2022/0152243 A1 May 19, 2022

(30) Foreign Application Priority Data
Apr. 5, 2019 (DK) ............................. PA201970218

(51) Int. Cl.
A61L 2/00 (2006.01)
A61L 2/10 (2006.01)
(Continued)

(52) U.S. Cl.
CPC ............. *A61L 2/10* (2013.01); *A61L 2103/15* (2026.01); *A61L 2202/11* (2013.01); *A61L 2202/122* (2013.01); *A61L 2202/123* (2013.01)

(58) Field of Classification Search
CPC ............ A61L 2/10; A61L 2/0047; A61L 2/08; A61M 1/285
(Continued)

(56) References Cited

U.S. PATENT DOCUMENTS

| | | | |
|---|---|---|---|
| 2003/0017073 A1 | 1/2003 | Eckhardt et al. | |
| 2010/0072399 A1* | 3/2010 | Street ........................ | A61L 2/10 250/492.1 |
| 2014/0334974 A1* | 11/2014 | Rasooly .................... | A61L 2/10 250/455.11 |

FOREIGN PATENT DOCUMENTS

| | | |
|---|---|---|
| CN | 108771778 A | 11/2018 |
| FR | 2799373 A1 | 4/2001 |

(Continued)

OTHER PUBLICATIONS

International Search Report and Written Opinion, dated Jun. 19, 2020, 16 pages, issued in PCT Application No. PCT/DK2020/050089.
(Continued)

*Primary Examiner* — Monzer R Chorbaji
(74) *Attorney, Agent, or Firm* — AVEK IP, LLC

(57) ABSTRACT

A sterilisation device for sterilising a section of a catheter tube includes a casing including a proximal end, a distal end, an attachment portion, a sterilisation chamber, and a through hole extending through the attachment portion and the sterilisation chamber, the through hole having a distal opening positioned at the distal end of the casing and leading into the sterilisation chamber, the attachment portion being configured to retain a section of a catheter tube in the through hole; and at least one light source configured to emit germicidal light into the sterilisation chamber of the casing. A diameter of the distal opening of the through hole is greater than a diameter of the through hole at the attachment portion, so that when the catheter tube is retained in the
(Continued)

through hole, an air gap is formed between the sterilisation chamber at the distal opening and the catheter tube.

20 Claims, 6 Drawing Sheets

(51) Int. Cl.
*A61N 5/00* (2006.01)
*G01N 23/00* (2006.01)
*A61L 103/15* (2026.01)

(58) Field of Classification Search
USPC ............................ 422/24; 250/492.1, 455.11
See application file for complete search history.

(56) References Cited

FOREIGN PATENT DOCUMENTS

| | | | |
|---|---|---|---|
| WO | 2002102421 | A1 | 12/2002 |
| WO | 2010036617 | A1 | 4/2010 |
| WO | 2011148009 | A1 | 12/2011 |
| WO | 2014120620 | A1 | 8/2014 |
| WO | 2018179676 | A1 | 10/2018 |

OTHER PUBLICATIONS

Search Report, dated Dec. 4, 2019, 7 pages, issued in Danish Application No. PA2019/70218.

* cited by examiner

Fig. 4a                    Fig. 4b

STERILISATION DEVICE FOR STERILISING A SECTION OF A CATHETER TUBE AND A METHOD FOR STERILISING A SECTION OF A CATHETER TUBE

CROSS-REFERENCE TO RELATED APPLICATIONS

This application is the U.S. national phase of, and claims priority to, International Application No. PCT/DK2020/050089, filed Apr. 3, 2020, which designated the U.S. and which claims priority to Danish Patent Application No. PA201970218 filed Apr. 5, 2019.

FIELD OF THE INVENTION

The invention relates to a sterilisation device for a catheter tube and to a method for sterilising a section of a catheter tube.

BACKGROUND

During various medical procedures, an artificial access way into the body of a patient is sometimes required, for instance to supply or remove fluids, administer pharmaceuticals, or to perform a wide variety of tasks. For this purpose, a catheter tube may be inserted through an opening of the body of the patient with an in vivo tubing section of the catheter tube positioned in vivo, i.e. inside the body of the patient, and an ex vivo tubing section positioned ex vivo, i.e. outside the body of the patient. In some cases, this catheter tube is kept in place in the patient for a prolonged period of time, which may allow germs to move along the inside and/or outside of the ex vivo tubing section to reach the in vivo tubing section and thus enter into the body of the patient, thereby risking an infection of the patient. To prevent this, a sterilisation device can be connected to the catheter tube to emit ultraviolet light at a germicidal intensity onto the ex vivo tubing section of the catheter tube, thereby sterilising and preventing infections. A drawback is that ultraviolet light at germicidal intensity is potentially carcinogenic to the patient. A light shield surrounding the ultraviolet light source is often employed to prevent excessive leakage of ultraviolet light to the outside, however it has been discovered that in some cases germs circumvent the germicidal light by moving on the outside of the light shield, thereby reducing the sterilising capability of the device. Additionally, as the patient sometimes needs to change position, the sterilisation device may end up underneath the patient with the potential to cause a bedsore or a pressure ulcer.

SUMMARY OF THE INVENTION

On this background, it may be seen as one object of the disclosure to provide a sterilisation device with an improved sterilising capability and/or where leakage of ultraviolet light is reduced to safe levels or even eliminated.

One or more of these objects may be met by the aspects of the disclosure as described in the following.

A first aspect of this disclosure relates to a sterilisation device for sterilising a section of a catheter tube. The sterilisation device includes a casing having a proximal end, a distal end, an attachment portion, a sterilisation chamber, and a through hole extending through both the attachment portion and the sterilisation chamber. The through hole has a distal opening positioned at the distal end of the casing and leads into the sterilisation chamber. The attachment portion is configured to retain a section of a catheter tube in the through hole. The device further includes at least one light source configured to emit germicidal light, such as ultraviolet light, into the sterilisation chamber of the casing. A diameter of the distal opening of the through hole is greater than a diameter of the through hole at the attachment portion of the casing, so that when the catheter tube is retained in the through hole by the attachment portion of the casing, an air gap is formed between the sterilisation chamber at the distal opening and the catheter tube.

An advantage of a sterilisation device according to this disclosure may be that germ circumvention of the sterilisation device is mitigated or eliminated as germs are prevented from crossing the air gap between the catheter tube and the distal opening of the sterilisation device, thus forcing the germs to move into the sterilisation chamber and be sterilised.

A tubing axis may extend from the proximal end of the casing to the distal end of the casing. The through hole may extend in parallel to the tubing axis.

The casing may comprise or consist essentially of a material, such as a polymer material, configured to absorb ultraviolet light at least at the same wavelength of the light emitted by the at least one light source. The casing may extend circumferentially around the tubing axis. The sterilisation chamber and/or the attachment portion of the casing may extend circumferentially around the tubing axis. The proximal end of the casing is intended to be oriented towards the patient and the distal end of the casing is intended to be oriented away from the patient. This may ensure that germs moving along the catheter tube towards the patient are sterilised before entering the patient.

The diameter of the through hole of the attachment portion may correspond substantially to the outer diameter of a catheter tube to be positioned in the through hole. The attachment portion may comprise at least one rib configured to retain a section of the catheter tube being positioned in the through hole. The attachment portion may be configured to axially retain and/or radially retain a section of a catheter tube positioned in the through hole.

The sterilisation chamber may be air filled, even when a catheter tube is positioned in the through hole.

The through hole may have a substantially circular cross-section perpendicular to the tubing axis substantially from the distal end of the through hole to the proximal end of the through hole. The tubing axis of the casing may form a centre line of the through hole.

The distal opening may be positioned at an end of the through hole. The distal opening may be positioned adjacent to the sterilisation chamber. The distal opening may lead directly to the sterilisation chamber. The distal opening may be substantially circular, so as to provide a substantially uniform radial extent of the air gap around the typically cylindrical catheter tube. The distal opening may be of substantially same shape as the catheter tube.

The distal opening may have a sufficiently large diameter in order to prevent germs to cross the air gap from the outer surface of the catheter tube to the casing.

In case of a non-constant through hole diameter at a specific location, the diameter of the through hole at said specific location, for instance the attachment portion or the distal opening, may be defined as the minimum diameter at said location.

The at least one light source may be a light emitting diode (LED) configured to emit germicidal light. The sterilisation device may additionally or alternatively comprise at least two, three, four, five, or even more light sources.

The at least one light source may be configured to emit ultraviolet light into the sterilisation chamber of the casing so as to sterilise the outer and inner surface of a section of a catheter tube positioned in the sterilisation chamber.

The sterilisation device may comprise a circuitry and/or a power source, such as one or more batteries. The circuitry may be connected to the at least one light source(s) and/or to the power source. The power source, such as a battery, may be configured for supplying power to the at least one light source.

The germicidal light emitted by the at least one light source may be ultraviolet light (UV), such as ultraviolet B (UVB) and/or ultraviolet C (UVC) light, with a wavelength in the range of 10-400 nm, or in the range of 100-400 nm, or in the range of 100-315 nm, in particular ultraviolet B (UVB) with a wavelength in the range of 305-315 nm or ultraviolet C (UVC) light with a wavelength in the range of 260-270 nm.

In the disclosure, a section of a tube may be understood as an axial section or longitudinal section of said tube.

In the disclosure, a catheter tube may be defined as a medical tube suitable for being connected to the body of a patient through a natural or artificial opening and may function as a drainage tube, a medicament administration tube, or a tubular access way for medical instruments.

Additionally or alternatively, the at least one light source may be positioned at a distance to the distal opening so that light directly emitted by the at least one light source is received by, or potentially received substantially only by, either the sterilisation chamber of the casing, or, if present, a catheter tube positioned in the through hole of the casing. This may provide the advantage that leakage of ultraviolet light out of the distal opening is reduced to safe levels or even eliminated.

Additionally or alternatively, the at least one light source may be positioned at a proximal end of the sterilisation chamber so that light directly emitted by the at least one light source is received by, or potentially received substantially only by, either the sterilisation chamber of the casing, or, if present, a catheter tube positioned in the through hole of the casing.

Additionally or alternatively, the at least one light source may be positioned so as to prevent light emitted from the at least one light source from leaking out of the distal opening.

Additionally or alternatively, the at least one light source may be configured so that a light ray of emitted light does not directly leak out of the distal opening.

Additionally or alternatively, a light well may be positioned between the at least one light source and the sterilisation chamber, so that light from the light source exiting the light well into the sterilisation chamber is substantially cylindrical.

Additionally or alternatively, the at least one light source may emit a plurality of light rays in a cone into the sterilisation chamber, wherein a perimeter of said cone does not directly intersect the distal opening, so that light does not directly leak of the distal opening.

In this disclosure, "directly" in relation to an emitted light ray may be defined as the straight line from the light source to the impact point of the emitted light ray, and thus may not mean reflected or refracted light rays.

Additionally or alternatively, the sterilisation chamber may comprise a wall surface extending between the at least one light source and the distal opening, wherein the distal opening forms a border of the wall surface, so that when the catheter tube is positioned in the through hole, a tubular air gap is formed between the wall surface and the catheter tube, wherein the tubular air gap extends from the distal opening and into the sterilisation chamber. This may provide the advantage, that the sterilising properties of the sterilisation device is improved since the air gap extends into the sterilisation chamber and thus germs are forced to move into the sterilisation chamber and be sterilised.

The wall surface may form an interior circumferentially and axially extending surface of the through hole.

Additionally or alternatively, the sterilisation device may comprise one or more centring member(s) configured to centre the catheter tube in the sterilisation chamber. This may improve the sterilising properties of the sterilisation device since the centring member(s) ensure(s) that the air gap extends all around the catheter tube, i.e. the catheter tube does not contact the distal opening or wall surface of the sterilisation chamber. This prevents germs from circumventing the sterilisation chamber.

The centring member(s) may be provided as a tubing holder further configured for attaching to the section of the catheter tube positioned in the sterilisation chamber, potentially by elastic deformation and/or clicking onto the section of the catheter tube. The centring member(s) may be fixed to and extend from the attachment portion of the casing, potentially as a cantilever beam. The centring member(s) may consist essentially of an UV translucent or preferably an UV transparent material.

Additionally or alternatively, the diameter of the distal opening may be at least 1.1 times the diameter of the through hole at the attachment portion, or of the diameter of the catheter tube that can be positioned in the through hole. The distal opening may be at least 1.1, 1.2, 1.3, 1.4, 1.5, 1.6, 1.7, 1.8, 1.9 or 2.0 times the diameter of the catheter tube that can be positioned in the through hole. This may improve the sterilising capability of the device as the risk of the catheter tube contacting the distal opening of the wall surface of sterilisation chamber is reduced with a larger diameter distal opening.

Additionally or alternatively, the sterilisation device may have an open position in which a catheter tube can be attached to the casing by the attachment portion of the casing, and/or a closed position in which a section of a catheter tube already present in the attachment portion of the casing can be retained. This may allow the sterilisation device to be attached to an ex vivo section of a catheter tube with a section already positioned in vivo of a patient, and thus increase the usability of the device.

Additionally or alternatively, the casing comprises, or consists of, two portions interconnected by a hinge, such as a living hinge, a pin-and-knuckle, or a floating hinge, the hinge being settable to the open position and the closed position, wherein a radial access way to the through hole is provided in the open position, so that a section of the catheter tube can be radially inserted into the through hole, and/or wherein the two portions of the casing surround the through hole in the closed position, so that the section of the catheter tube already present in the attachment portion of the casing can be at least radially retained. This may provide the advantage of a particularly mechanically simple arrangement.

The two portions may be positioned at a distance to each other in the open position.

The hinge may be a living hinge, which may be a particularly suited for this purpose as it is easier to clean the hinge. The hinge may alternatively be a pin-and-knuckle hinge or a floating hinge.

In the open position, a radial access way may be provided to the through hole, so that a catheter tube can be radially inserted into the through hole.

Additionally or alternatively, the two portions of the casing may be in the form of halves of the casing and be movable around a hinge axis of the hinge, the hinge axis being parallel to a tubing axis of the through hole.

Additionally or alternatively, the sterilisation device may comprise a control device and a detection device, wherein the control device is configured to cause the at least one light source to start emitting germicidal light when the detector device detects that the casing is in the closed position, and/or wherein the control device is configured to cause the at least one light source to stop emitting germicidal light when detector device detects that the casing is in the open position.

The advantage of starting emission of light in the closed position may include improving the sterilising capability of the device as it is not necessary to switch the device on once fitted onto a catheter tube. The advantage of stopping emission of light in the open position may include preventing leakage of ultraviolet light with potentially carcinogenic effects as well as saving energy.

Additionally or alternatively, the sterilisation device comprises a control device and a detection device, wherein the control device is configured to cause the at least one light source to start emitting germicidal light when the detector device detects that the casing is attached to the catheter tube and/or is in the closed position, and/or wherein the control device is configured to cause the at least one light source to stop emitting germicidal light when the detector device detects that the casing is detached from the catheter tube and/or is in the open position.

Additionally or alternatively, the sterilisation device comprises a control device and a detection device, wherein the control device is configured to cause the at least one light source to start emitting germicidal light when the detector device detects that the casing is attached to the catheter tube, and/or wherein the control device is configured to cause the at least one light source to stop emitting germicidal light when detector device detects that the casing is detached from the catheter tube.

Additionally or alternatively, the detection device may comprise a pin and the control device may comprise a switch, wherein the pin contacts the switch when the casing is in the closed position and causes the at least one light source to start emitting germicidal light, and wherein the pin is positioned at a distance to the switch when the casing is in the open position and causes the at least one light source to stop emitting germicidal light.

The detection device may create a first signal indicating the closed position when the pin contacts the switch. The detection device may create a second signal indicating the open position when the pin does not contact the switch. The detection device may provide the first and/or second signal to the control device controlling the emission of light from the at least one light source. The pin may be positioned on one portion of the casing and the switch may be positioned on another portion of the casing.

Additionally or alternatively, the casing may have an outer surface configured to face the exterior of the sterilisation device, the outer surface having a streamlined, curved shape. This may provide the advantage of minimizing the risk of the patient developing pressure ulcers due to the patient lying or sitting on the device.

Additionally or alternatively, the outer surface of the casing may not comprise discontinuities, such as edges.

Additionally or alternatively, the outer surface of the casing may have streamlined shape and/or a curved shape potentially along an axial extent of the casing from the proximal end to the distal end and/or along a circumferential extent of the casing.

Additionally or alternatively, the outer surface of the casing may comprise, potentially an exterior layer of, a material that may be softer relative to an interior portion of the casing. The material may be an elastomer, such as a rubber.

Additionally or alternatively, a maximum axial length of the sterilisation device, potentially along the tubing axis, from the proximal end to the distal end is at least 1.1, 1.2, 1.3, or 1.4 times a maximum outer diameter of the sterilisation device.

Additionally or alternatively, the sterilisation device may have a maximum outer diameter around the tubing axis and a length extending along the central axis, wherein the length is at least 1.1, 1.2, 1.3, or 1.4 times the maximum outer diameter.

The sterilisation device may comprise a proximal part consisting of a soft, resilient material, such as foam or silicone. This will allow attachment of the sterilisation device on the catheter close to the opening in a patient's body through which the catheter enters the body. The softness and resilience of the material means that the risk of irritation and pressure ulcers due to contact with the sterilization device is reduced, thus allowing it to be positioned closer to the body than what would be the case with a sterilization device without such a proximal part. The section of the catheter tube extending from the sterilisation device to the body and thus the area on the catheter where the bacteria can by-pass the device can thus be minimized.

In addition, the provision of the proximal part made from a soft, resilient material may reduce the displacement of the device and the catheter tube when the patient moves etc. In other words, the risk of the catheter tube unintentionally moving further in through the opening in the patient's body or out of it is reduced, which again may reduce the risk of an infection.

The soft and resilient material may for example be a foamed polymer, such as polyurethane, or silicone.

To further reduce the risk of infection, the proximal part or the entire sterilisation device may be coated with an antibacterial or bacteria-repellent coating.

The proximal part may consist of two halves, which can be connected to each other by means of glue, adhesive, or tape when the sterilisation device is attached to the catheter tube. This is particularly advantageous when the rest of the sterilisation device also comprises two halves. A cover sheet may be provided for protecting the glue, adhesive, or tape until it is to be used. The proximal part and/or the main body of the sterilisation device may, however, also be made in one part or from more three or more interconnected components.

A UV reflection zone may be provided in the sterilization chamber. By reflecting ultraviolet light, it will increase the UV exposure and thereby potentially increase the efficiency of the sterilisation.

The sterilisation device may form part of a kit of parts, which may further comprise a catheter tube, wherein the sterilisation device is positioned around a section of the catheter tube and the diameter of the distal opening is greater than the outer diameter of the catheter tube.

The section of the catheter tube around which the sterilisation device is positioned may be an ex vivo section of the catheter tube.

Such a kit of parts may provide the advantage that germs moving along the catheter tube is prevented from circumventing the sterilisation device as germs are prevented from crossing the air gap between the catheter tube and the distal opening of the sterilisation device thus forcing the germs to move into the sterilisation chamber and be sterilised.

A second aspect of this disclosure relates to a method for sterilising a section of a catheter tube, the method comprising the steps of: providing a sterilisation device according to the first aspect and a catheter tube; positioning a section of the catheter tube in the through hole of the sterilisation device; and causing the at least one light source to emit germicidal light onto a section of the catheter tube, thereby sterilising said section of the catheter tube.

An advantage of such a method may be that germ circumvention of the sterilisation device is mitigated or eliminated as germs are prevented from crossing the air gap between the catheter tube and the distal opening of the sterilisation device thus forcing the germs to move into the sterilisation chamber and be sterilised.

The step of positioning a section of the catheter tube in the through hole of the sterilisation device may comprise a, potentially prior, step of setting the sterilisation device to the open position, and/or a, potentially posterior, step of setting the sterilisation device to the closed position.

A third aspect of this disclosure relates to the use of a sterilising device according to the first aspect for sterilising a section of a catheter tube.

The sterilisation device according to the invention may potentially be used on any catheter tube entering through an opening in the body of a human or animal. It is presently considered to be particularly advantageous for use on catheter tubes entering a urethra, a blood vessel, an abdominal cavity, a pelvic cavity, a thoracic cavity, a cranial cavity, a spinal cavity, a tracheal tube, or subcutaneous.

A person skilled in the art will appreciate that any one or more of the above aspects of this disclosure and embodiments thereof may be combined with any one or more of the other aspects of this disclosure and embodiments thereof.

BRIEF DESCRIPTION OF THE DRAWINGS

In the following, non-limiting exemplary embodiments are described detailing the aspect(s) of the disclosure with reference to the drawings, where.

DETAILED DESCRIPTION

Figure 1:
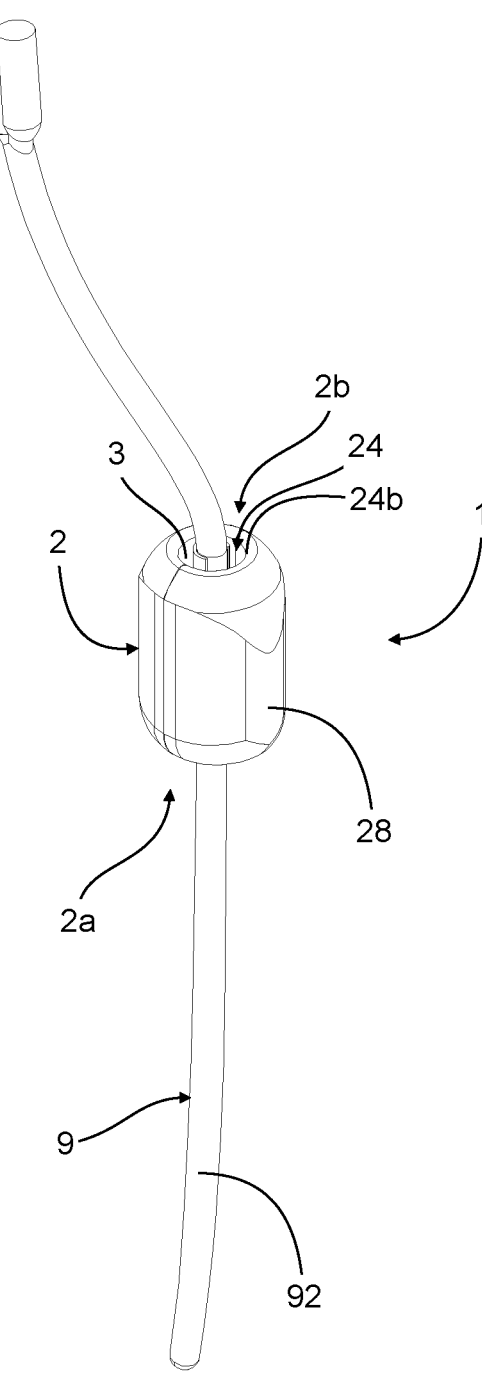
FIG. 1 shows a perspective view of a sterilisation device attached to a section of a catheter tube.
Figures 2A, 2B, 2C:
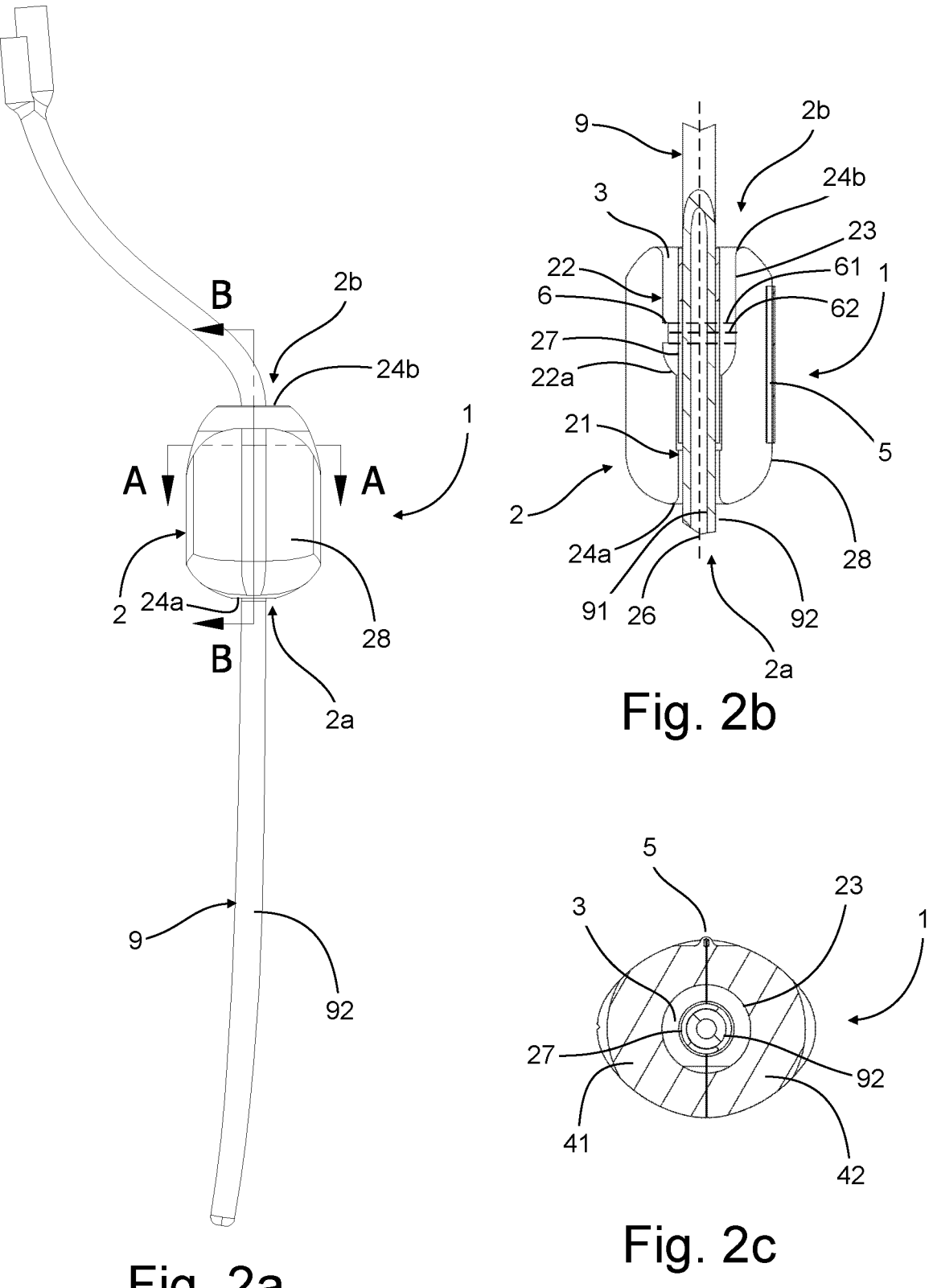
FIG. 2a shows a side view of the sterilisation device and catheter tube of FIG. 1.
FIG. 2b shows a side cross-sectional view of the sterilisation device and catheter tube along cross-sectional line B-B of FIG. 2a, FIG. 2c shows an axial cross-sectional view of the sterilisation device and catheter tube along cross-sectional line A-A of FIG. 2a, FIG. 3 shows a perspective view of a sterilisation device in an open position without a catheter tube.

Referring first to FIGS. 1 and 2a, a sterilisation device 1 is shown with a catheter tube 9 extending there through. The sterilisation device 1 comprises a casing 2 with a proximal end 2a, a distal end 2b, and an outer surface 28. The proximal end 2a of the casing 2 is intended to be oriented towards a patient and the distal end 2b of the casing 2 is intended to be oriented away from the patient. The outer surface 28 of the casing 2 is facing the exterior of the sterilisation device 1 and has a streamlined, curved shape from the proximal end 2a to the distal end 2b without sharp edges or corners in order to prevent causing a pressure ulcer if the sterilisation device 1 should end up beneath the patient. The maximum axial length of the sterilisation device 1 from the proximal end 2a to the distal end 2b is about 1.5 times the maximum outer diameter of the sterilisation device 1.

The casing 2 comprises a through hole 24 with a circular proximal opening 24a located at the proximal end 2a of the casing 2 and a circular distal opening 24b located at the distal end 2b of the casing 2. A diameter of the distal opening 24b of the through hole 24 is greater than the outer diameter of the catheter tube 9, so that an air gap 3 is formed between the distal opening 24b and the catheter tube 9 as can be seen on FIG. 1.

Turning to FIG. 2b, a tubing axis 26 extends from the proximal end 2a of the casing 2 to the distal end 2b of the casing 2. The tubing axis 26 of the casing 2 forms a centre line of the through hole 24. The through hole 24 has a circular cross-section perpendicular to the tubing axis 26 from the distal opening 24b at the distal end 2b of the casing 2 to the proximal opening 24a at the proximal end 2a of the through hole 24.

The casing 2 comprises an attachment portion 21, a sterilisation chamber 22, and the through hole 24 extending through both the attachment portion 21 and the sterilisation chamber 22. The through hole 24 comprises the distal opening 24b which is positioned at the distal end 2b of the casing 2 adjacent to and leading directly into the sterilisation chamber 22. A section of a catheter tube 9 is retained in the through hole 24 by the attachment portion and a centring member 27.

The sterilisation chamber 22 comprises a wall surface 23 extending between the light source 6 and the distal opening 24b. The wall surface 23 forms an interior circumferentially and axially extending surface of the through hole 24. The distal opening 24b forms a border of the wall surface 23. The air gap 3 extends with a tubular shape between the wall surface 23 and the outer surface 92 of the catheter tube 9 from the distal opening 24b into the sterilisation chamber 22 towards the light source 6.

Turning to FIG. 2c, the air gap 3 has uniform radial extent around the cylindrical catheter tube 9. The diameter of the distal opening 24b is about 2 times the outer diameter of the catheter tube 9, this ensures that the air gap 3 is sufficiently large in order to prevent germs crossing the air gap 3 from the outer surface 92 of the catheter tube 9 to the outer surface 28 of the casing 2.

Figure 3:
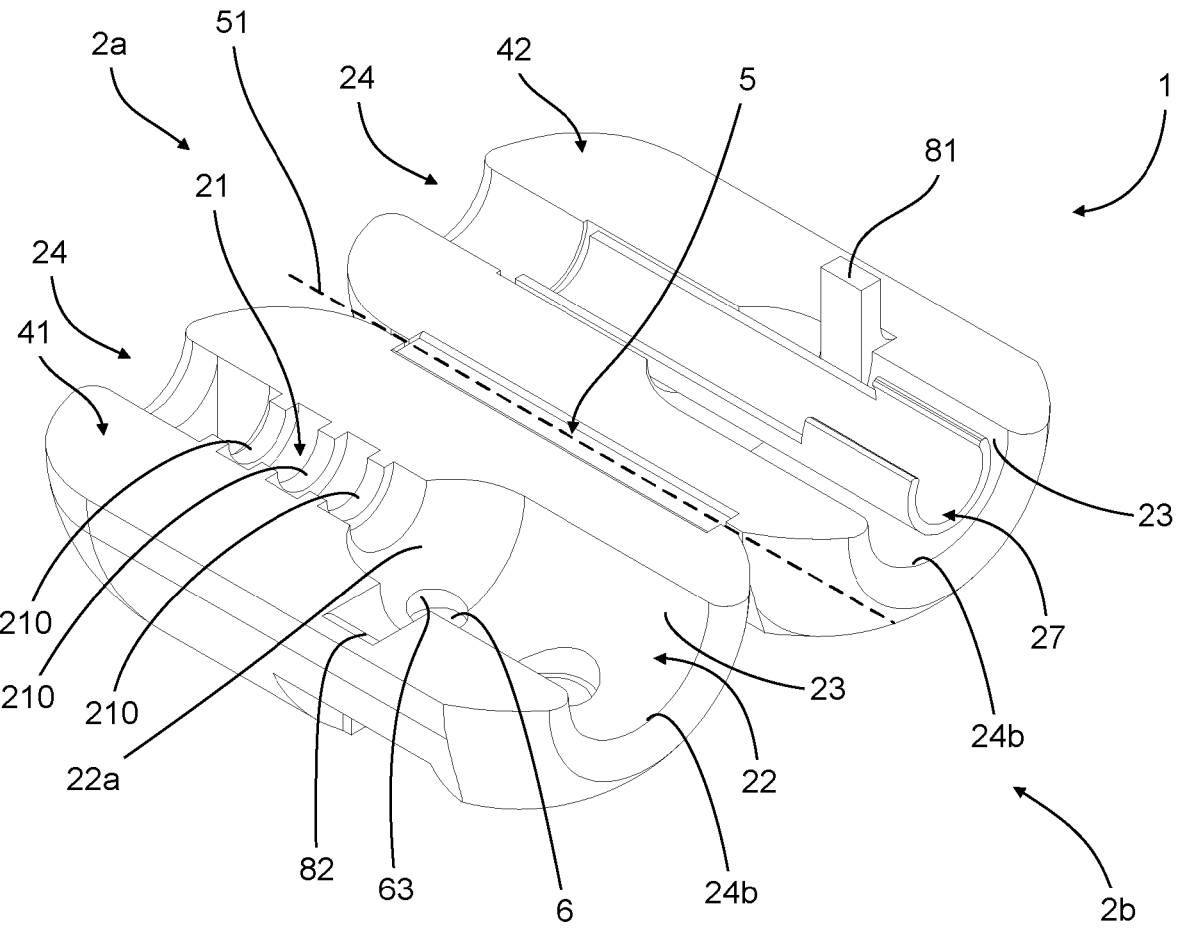

Referring now to FIG. 3 the sterilisation device 1 is shown in an open position. The casing 2 comprises a floating hinge 5 interconnecting a first half 41 and a second half 42 of the casing 2. The halves 41, 42 of the casing 2 are movable around a hinge axis 51 of the hinge 5, which is parallel to the tubing axis 26. The hinge 5 allows the sterilisation device 1 to be set in the open position as shown in FIGS. 3 and 4a-4c, and in a closed position as shown in FIGS. 1 and 2a-2c. The open position provides radial access way to the through hole 24 so that a section of the catheter tube 9 can be radially inserted into the through hole 24 and attached to the casing 2 by the attachment portion 21 of the casing 2. In the closed position, the two halves 41, 42 radially surround catheter tube 9 in the through hole 24 so as to radially retain the catheter tube 9 in the through hole 24.

The sterilisation device 1 further comprises a centring member 27 in the form of a tubing holder as seen in FIG. 3. The centring member 27 attaches to the catheter tube 9 by elastically deforming and snapping onto the outer surface 92 of the catheter tube 9. The centring member 27 is fixed to the casing 2 at a proximal end 22a of the sterilisation chamber 22 and extends into the sterilisation chamber 22 thereby forming a cantilever beam. The centring member 27 biases the catheter tube 9 towards the centre line, i.e. the tubing axis 26, of the sterilisation chamber 22 as best seen in FIG. 2b. The centring member 27 consist essentially of an ultraviolet translucent or ultraviolet transparent material.

The attachment portion 21 comprises three ribs 210 configured to retain a section of the catheter tube 9 being positioned in the through hole 24. The diameter of the distal opening 24b of the through hole 24 is greater than a diameter of the through hole 24 at the ribs 210 of the attachment portion 21 of the casing 2, so that when the catheter tube 9 is retained in the through hole 24 by the attachment portion 21 of the casing 2, an air gap 3 is formed between the sterilisation chamber 22 at the distal opening 24b and the catheter tube 9 as can be seen between the centring member 27 and the wall surface 23 of the sterilisation chamber 22.

Figure 4C:
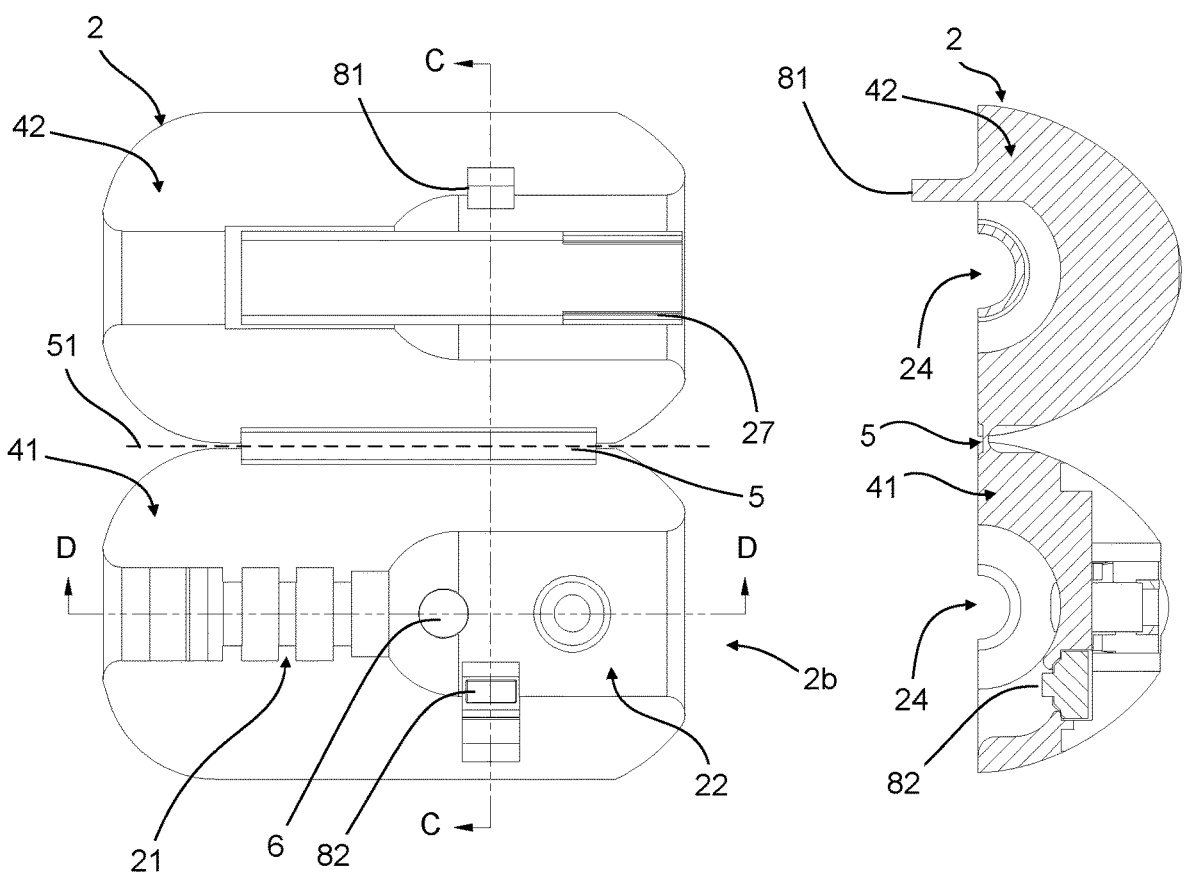
FIG. 4a shows a side view of the sterilisation device of FIG. 3.
FIG. 4b shows a cross-sectional view of the sterilisation device along cross-sectional line C-C of FIG. 4a, FIG. 4c shows a cross-sectional view of the sterilisation device along cross-sectional line D-D of FIG. 4a, FIG. 5 corresponds to FIG. 1 but showing a different embodiment of the invention, FIG. 6 corresponds to FIG. 3 but showing the embodiment in FIG. 5.
Figure 4C:
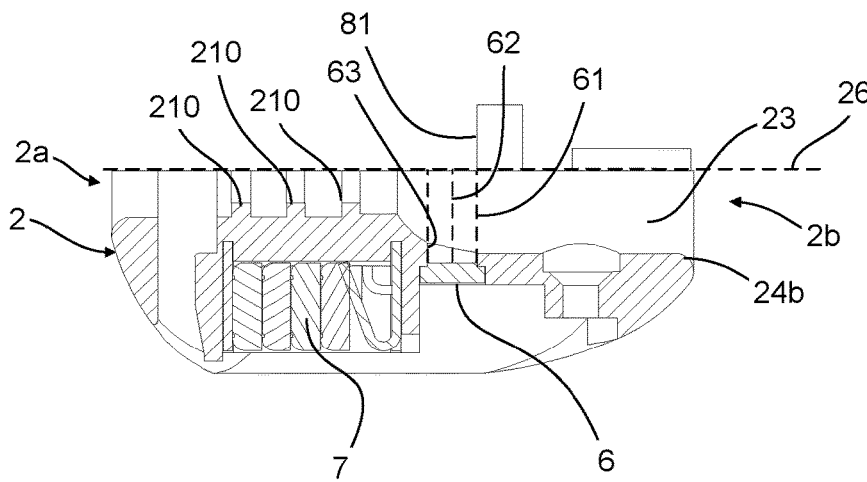

The light source 6 is in the form of a light emitting diode configured to emit germicidal ultraviolet light C (UVC) light with a wavelength in the range of 100-280 nm into the sterilisation chamber 22 of the casing 2. The light source 6 is positioned at the proximal end 22a of the sterilisation chamber 22 so as to be positioned as far away from the distal opening 24b while still ensuring sufficient sterilisation of the catheter tube 9. The wall surface 23 of the sterilisation chamber 22 consist essentially of a polymer material configured to at least partially absorb ultraviolet C light. The light source 6 is positioned in a light well 63 as best seen in FIGS. 3 and 4c which ensures that light emitted from the light source 6 exits the light well 63 substantially in a light cylinder 62 around the optical axis 62 of the light source 6. The optical axis 62 of the light source 6 is substantially perpendicular to the tubing axis as seen on FIG. 4c, so that the light rays directly emitted by the light source 6 is received and at least partially absorbed by the opposite side of the wall surface 25 of the sterilisation chamber 22, the centring member 27, or the outer surface 92 of the catheter tube 9. This has the advantage that the intensity of the ultraviolet light is reduced to safe levels at the distal opening 24b of the through hole 24.

As best seen in FIGS. 4a-4c, the sterilisation device 1 further comprises a detection device 81 in the form of a pin, a control device 82 in the form of a switch, circuitry (not shown) and a power source 7 in the form of a battery. The circuitry interconnects the control device 82, the light source 6, and the power source 7. The power source is configured for supplying power to the circuitry and thereby the light source 6. The detection device 81 is positioned on the second half 42 of the casing 2 and the control device 82 is positioned on the first half 41 of the casing 2.

In the open position, as shown in FIG. 3, the detection device 81 is positioned at a distance to the control device 82 which disconnects the power source 7 from the light source 6 causing the light source 6 to stop emitting the germicidal light.

In the closed position, as shown in FIGS. 1 and 2a-2c, the detection device 81 contacts the control device 82 connecting the power source 7 to the light source 6, causing the light source 6 to start emitting the germicidal light.

Figure 5:
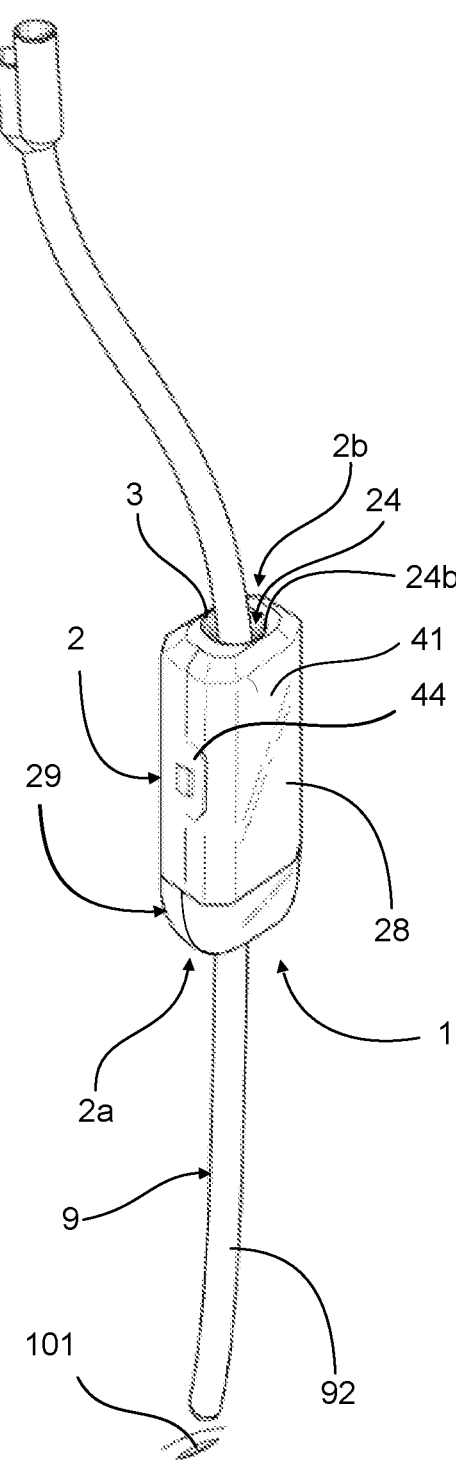
Figures 6, 7:
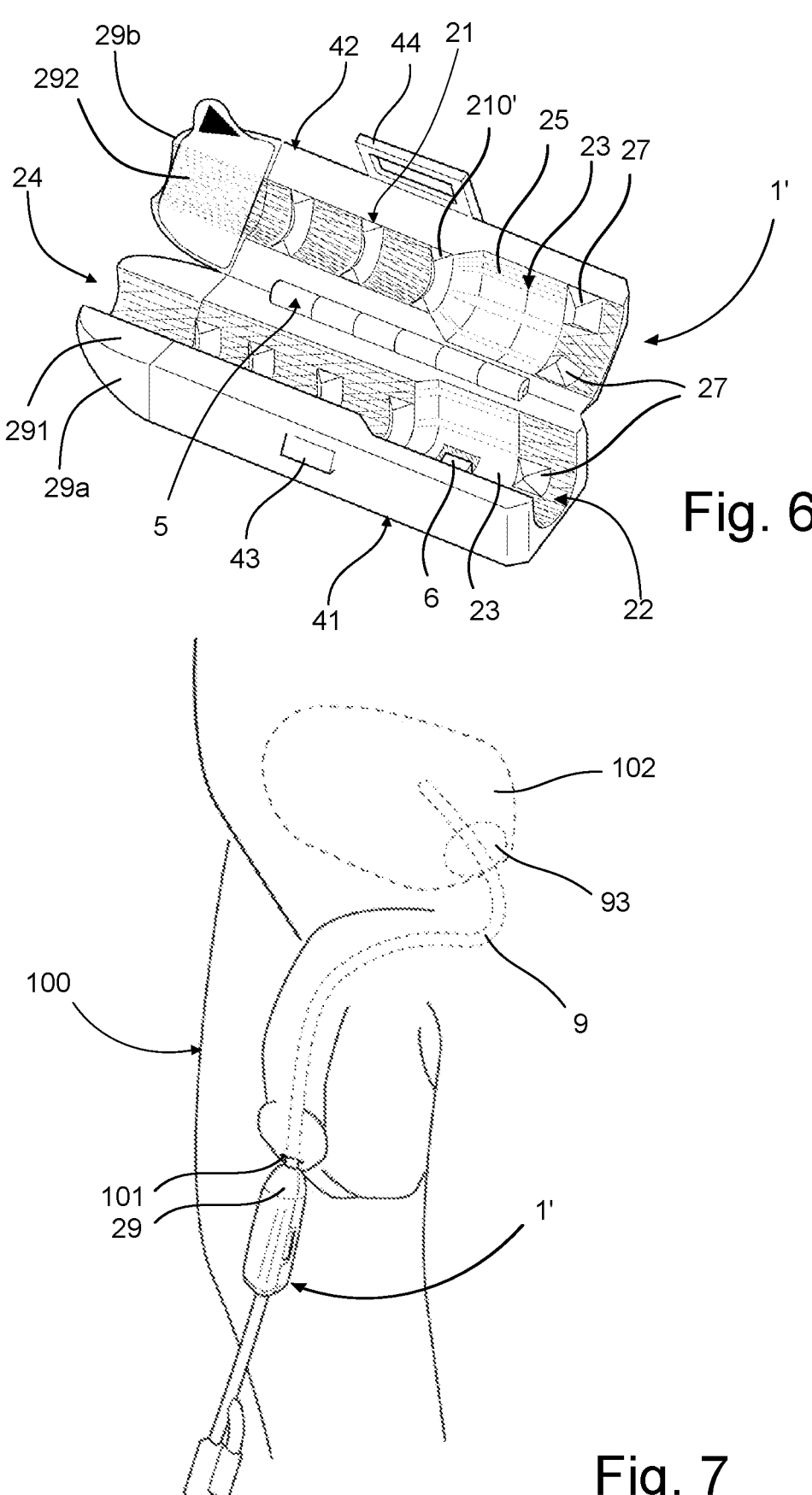
FIG. 7 shows the sterilization device in FIGS. 5 and 6 when in use on a urinary catheter.

A different embodiment of a sterilisation device 1' is shown in FIGS. 5-7. In these figures and in the description relating thereto, the same reference numbers are used as in FIGS. 1-4 for features having the same function even though they are not necessarily identical. In order to avoid undue repetition only the differences between this embodiment and what was described with reference to FIG. 1-4 will be described in detail.

FIG. 5 shows a sterilisation device 1' mounted on a catheter tube 9 and in FIG. 6 the sterilisation device is shown in an opened position. As may be seen, this sterilisation device 1' is of a less rounded outer shape than the sterilisation device 1 in FIGS. 1-4.

In order to be able to attach the sterilisation device 1' on the catheter tube 9 as close to the opening 101 in the patient's body 100 as possible and thereby minimize the area on the catheter tube via which bacteria can by-pass the device, a soft, resilient foam/silicone material in the form of a proximal part 29 has been added at the proximal end of the device. The proximal part positioned close to the body 100 of a patient and on a catheter inserted through an opening 101 in the body is shown in FIG. 7. In FIG. 7 the catheter tube 9 is a urinary catheter inserted in the urethra of a male patient, but it may be used for a female patient or for a different type of catheter, such as an abdominal catheter.

The provision of the proximal part 29 reduces the risk of the sterilisation device 1' inflicting a pressure on the patient's body, which may be particularly unpleasant when used at the genitalia as shown in FIG. 7 and which may also result in skin damages and hence an increased risk of infection.

Another advantage of the soft and resilient proximal part 29 is that the risk of the catheter tube 9 being pulled or pushed on when the patient moves is reduced. In the example in FIG. 7 the catheter tube 9 is being held in place in the urinary bladder 102 of the patient by means of a balloon 93 arranged on the section of the catheter tube extending into urinary bladder. The balloon prevents the catheter tube 9 from being pulled out, but does not prevent it from being pushed further in. The provision of the proximal part 29 allows the sterilisation device 1' to be positioned very close to the opening in the patient's body, in this case down to about 1 mm from the opening, and this in itself reduces the risk of the catheter tube being pushed inwards. In addition, the resilience of the material of the proximal part 29 means that it may compensate for some movements.

As described above with reference to FIG. 3 the sterilisation device 1' in FIGS. 5-7 also consists of two halves 41, 42, which are interconnected at a hinge 5 as may be seen in FIG. 6. The proximal part 29 is also consisting of two halves 29a, 29b each associated with a respective half 41, 42 of the device.

To ensure that the sterilisation device 1' closes tightly around the catheter tube 9, a male lock part 43 is provided in the first half 41 and a female lock part 44 is provided on the second half 42. When moving the sterilisation device from the open position in FIG. 6 to the closed position in FIG. 5 these two lock parts will snap-lock to each other. In addition, one half 29*b* of proximal part 29 is provided with an adhesive (not visible), which is covered by a cover sheet 292. Before closing the sterilisation device 1' around the catheter tube 9, the cover sheet is to be removed so that the two halves 29*a*, 29*b* of the proximal part 29 adhere to each other in the closed position.

Other means for locking the two halves 41, 42 to each other and/or for connecting the two halves 29*a*, 29*b* of the proximal part are also possible, including the use of tape and hook-and-loop type fasteners, such as Velcro.

As may be seen in FIG. 6 this embodiment of the sterilisation device 1' comprises a series of centring members 27 projecting from the inner wall surface 23 at the distal end. Each of these centring members 27 contact the catheter tube 9 and contributes to keeping it centred with the sterilisation device. An advantage of using these centring members is that the contact area with the catheter tube is small.

The embodiment in FIG. 5-7 comprises a UV reflection zone 25 on the inner wall surface 23, said zone extending from the rib marked 210' of the attachment portion 21 to the centring members 27. The surface of the UV reflection zone is made from a material, which reflects UV radiation. Due to the reflection of the UV light emitted by the light source 6, the catheter tube 9 extending through the sterilisation chamber 22 will be subjected to an increased UV exposure compared to if using a corresponding sterilisation device without a UV reflection zone.

The following is a list of reference numerals used throughout this specification. In case of any doubt, the reference numerals of the following list apply.

1 sterilisation device
  2 casing
  2*a* proximal end
  2*b* distal end
  21 attachment portion
  210 rib
  22 sterilisation chamber
  22*a* proximal end
  23 wall surface
  24 through hole
  24*a* proximal opening
  24*b* distal opening
  25 reflection zone
  26 tubing axis
  27 centring member
  28 outer surface
  29 proximal part
  29*a* first half of proximal part
  29*b* second half of proximal part
  291 contact surface of proximal part
  292 cover sheet on proximal part
  3 air gap
  41 first half
  42 second half
  43 lock part on first half
  44 lock part on second half
  5 hinge
  51 hinge axis
  6 light source
  61 light cylinder
  62 optical axis
  63 light well
  7 power source
  81 detection device
  82 control device
  9 catheter tube

91 inner surface
  92 outer surface
  93 balloon
  100 body of patient
  101 opening in patient
  102 urinary bladder

The invention claimed is:

1. A sterilisation device for sterilising a section of a catheter tube, the sterilisation device comprising:
  a casing including a proximal end, a distal end, an attachment portion, a sterilisation chamber, and a through hole extending through both the attachment portion and the sterilisation chamber, the through hole having a distal opening positioned at the distal end of the casing and leading into the sterilisation chamber, the attachment portion being configured to retain a section of a catheter tube in the through hole; and
  at least one light source configured to emit germicidal light into the sterilisation chamber of the casing;
  wherein the sterilisation chamber comprises a wall surface extending between the at least one light source and the distal opening, the wall surface forming an interior circumferentially and axially extending surface of the through hole;
  wherein the wall surface includes a tapered portion such that an inner diameter of the through hole defined by the wall surface decreases along the tapered portion in a direction from the distal opening toward the attachment portion; and
  wherein a diameter of the distal opening of the through hole is greater than a diameter of the through hole at the attachment portion of the casing, so that when the catheter tube is retained in the through hole by the attachment portion of the casing, an air gap is formed between the sterilisation chamber at the distal opening and the catheter tube, the air gap extending completely axially around the catheter tube.

2. The sterilisation device according to claim 1, wherein the at least one light source is positioned at a distance to the distal opening so that light directly emitted by the at least one light source is received by at least one of the sterilisation chamber of the casing, and a catheter tube positioned in the through hole of the casing.

3. The sterilisation device according to claim 1, wherein:
  the distal opening forms a border of the wall surface, so that when the catheter tube is positioned in the through hole, a tubular air gap is formed between the wall surface and the catheter tube; and
  the tubular air gap extends from the distal opening and into the sterilisation chamber.

4. The sterilisation device according to claim 3, further comprising a centring member configured to centre the catheter tube in the sterilisation chamber.

5. The sterilisation device according to claim 1, further comprising a centring member configured to centre the catheter tube in the sterilisation chamber.

6. The sterilisation device according to claim 1, wherein the diameter of the distal opening is at least 1.1 times the diameter of the through hole at the attachment portion or of the diameter of the catheter tube that can be positioned in the through hole.

7. The sterilisation device according to claim 1, wherein the sterilisation device is configured to alternate between:
  an open position in which a catheter tube can be attached to the casing by the attachment portion of the casing, and a closed position in which a section of a catheter tube already present in the attachment portion of the casing can be retained.

8. The sterilisation device according to claim 7, wherein:

the casing comprises two portions interconnected by a hinge, the hinge being settable to the open position and the closed position;

a radial access way to the through hole is provided in the open position, so that a section of the catheter tube can be radially inserted into the through hole; and the two portions of the casing surround the through hole in the closed position, so that the section of the catheter tube already present in the attachment portion of the casing can be at least radially retained.

9. The sterilisation device of claim 8, wherein the hinge is a living hinge, a pin-and-knuckle, or a floating hinge.

10. The sterilisation device according to claim 7, wherein:

the casing comprises two portions interconnected by a hinge, the hinge being settable to the open position and the closed position;

a radial access way to the through hole is provided in the open position, so that a section of the catheter tube can be radially inserted into the through hole; or the two portions of the casing surround the through hole in the closed position, so that the section of the catheter tube already present in the attachment portion of the casing can be at least radially retained.

11. The sterilisation device according to claim 1, wherein:

the sterilisation device comprises a control device and a detection device;

the control device is configured to cause the at least one light source to start emitting germicidal light when the detection device detects that the casing is in a closed position; and the control device is configured to cause the at least one light source to stop emitting germicidal light when the detection device detects that the casing is in an open position.

12. The sterilisation device according to claim 1, wherein the casing has an outer surface configured to face an exterior of the sterilisation device, the outer surface having a streamlined, curved shape.

13. The sterilisation device according to claim 1, wherein a maximum axial length of the sterilisation device from the proximal end to the distal end is at least 1.1 times a maximum outer diameter of the sterilisation device.

14. The sterilisation device according to claim 1, further comprising a proximal part consisting of a soft, resilient material.

15. The sterilisation device according to claim 14, wherein the soft, resilient material is foam or silicone.

16. The sterilisation device according to claim 1, further comprising an antibacterial or bacteria-repellent coating.

17. The sterilisation device according to claim 1, wherein a UV reflection zone is provided in the sterilisation chamber.

18. The sterilisation device of claim 1, wherein the germicidal light is ultraviolet light.

19. The sterilisation device according to claim 1, wherein:

the sterilisation device comprises a control device and a detection device;

the control device is configured to cause the at least one light source to start emitting germicidal light when the detection device detects that the casing is in a closed position; or the control device is configured to cause the at least one light source to stop emitting germicidal light when the detection device detects that the casing is in an open position.

20. A method for sterilising a section of a catheter tube, the method comprising the steps of:

providing a sterilisation device, comprising:

a casing including a proximal end, a distal end, an attachment portion, a sterilisation chamber, and a through hole extending through both the attachment portion and the sterilisation chamber, the through hole having a distal opening positioned at the distal end of the casing and leading into the sterilisation chamber, the attachment portion being configured to retain a section of a catheter tube in the through hole; and at least one light source configured to emit germicidal light into the sterilisation chamber of the casing;

wherein the sterilisation chamber comprises a wall surface extending between the at least one light source and the distal opening, the wall surface forming an interior circumferentially and axially extending surface of the through hole;

wherein the wall surface includes a tapered portion such that an inner diameter of the through hole defined by the wall surface decreases along the tapered portion in a direction from the distal opening toward the attachment portion, thereby defining a generally funnel-shaped portion of the through hole; and wherein a diameter of the distal opening of the through hole is greater than a diameter of the through hole at the attachment portion of the casing, so that when the catheter tube is retained in the through hole by the attachment portion of the casing, an air gap is formed between the sterilisation chamber at the distal opening and the catheter tube, the air gap extending completely axially around the catheter tube;

positioning a section of the catheter tube in the through hole of the sterilisation device; and actuating the at least one light source to emit germicidal light onto a section of the catheter tube, thereby sterilising said section of the catheter tube.

* * * * *